(12) United States Patent
Szczesnowicz et al.

(10) Patent No.: US 11,906,504 B2
(45) Date of Patent: Feb. 20, 2024

(54) ELECTROMAGNETIC CHIP DETECTOR

(71) Applicant: PRATT & WHITNEY CANADA CORP., Longueuil (CA)

(72) Inventors: Piotr Szczesnowicz, Brampton (CA); Michael Paul Smith, Mississauga (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 214 days.

(21) Appl. No.: 17/577,190

(22) Filed: Jan. 17, 2022

(65) Prior Publication Data
US 2023/0228731 A1    Jul. 20, 2023

(51) Int. Cl.
   *G01N 33/28*      (2006.01)
   *G01N 15/06*      (2006.01)

(52) U.S. Cl.
   CPC ..... *G01N 33/2858* (2013.01); *G01N 15/0656* (2013.01)

(58) Field of Classification Search
CPC ........... G01N 15/0606; G01N 15/0656; G01N 2015/0053; G01N 33/2858; G01N 27/08
See application file for complete search history.

(56) References Cited

U.S. PATENT DOCUMENTS

| | | | | |
|---|---|---|---|---|
| 5,179,346 | A | * | 1/1993 | McGee ............... G01N 15/0656 324/693 |
| 5,674,401 | A | * | 10/1997 | Dickert ............... G01N 33/2888 210/695 |
| 10,197,488 | B2 | | 2/2019 | Youssef |
| 10,866,201 | B2 | | 12/2020 | Best |
| 2018/0030850 | A1 | * | 2/2018 | Hagen ..................... F16N 29/04 |
| 2018/0275083 | A1 | * | 9/2018 | Kiriyama ........... G01N 33/2858 |

(Continued)

FOREIGN PATENT DOCUMENTS

| | | |
|---|---|---|
| DE | 102017204304 A1 | 9/2018 |
| EP | 3888792 A1 | 10/2021 |

OTHER PUBLICATIONS

European Patent Office, Communication re. extended European search report for European patent application No. 23151999.2, dated Apr. 28, 2023.

(Continued)

*Primary Examiner* — Alvaro E Fortich
*Assistant Examiner* — Adam S Clarke
(74) *Attorney, Agent, or Firm* — NORTON ROSE FULBRIGHT CANADA LLP

(57) ABSTRACT

Electromagnetic chip detectors and associated methods of detecting a metallic chip in engine fluid of an engine are provided. The method comprises supplying an electric current to a circuit extending between a first node and a second node to magnetize both a first electrically conductive terminal and a second electrically conductive terminal spaced apart from each other to define a chip-receiving gap therebetween, and detecting a change in resistance across the first node and the second node. The change in resistance is indicative of a capture of the chip by the electromagnetic chip detector. The chip electrically connects the first electrically conductive terminal to the second electrically conductive terminal. The first electrically conductive terminal is electrically connected to the first node. The second electrically conductive terminal is electrically connected to the second node.

20 Claims, 7 Drawing Sheets

(56) References Cited

U.S. PATENT DOCUMENTS

2021/0262897 A1  8/2021  Shenouda
2021/0263009 A1  8/2021  Shenouda

OTHER PUBLICATIONS

English translation of European document No. 3888792 dated Oct. 6, 2021, https://patents.google.com/patent/EP3888792A1/en?oq=EP3888792, accessed on Jan. 10, 2022.

\* cited by examiner

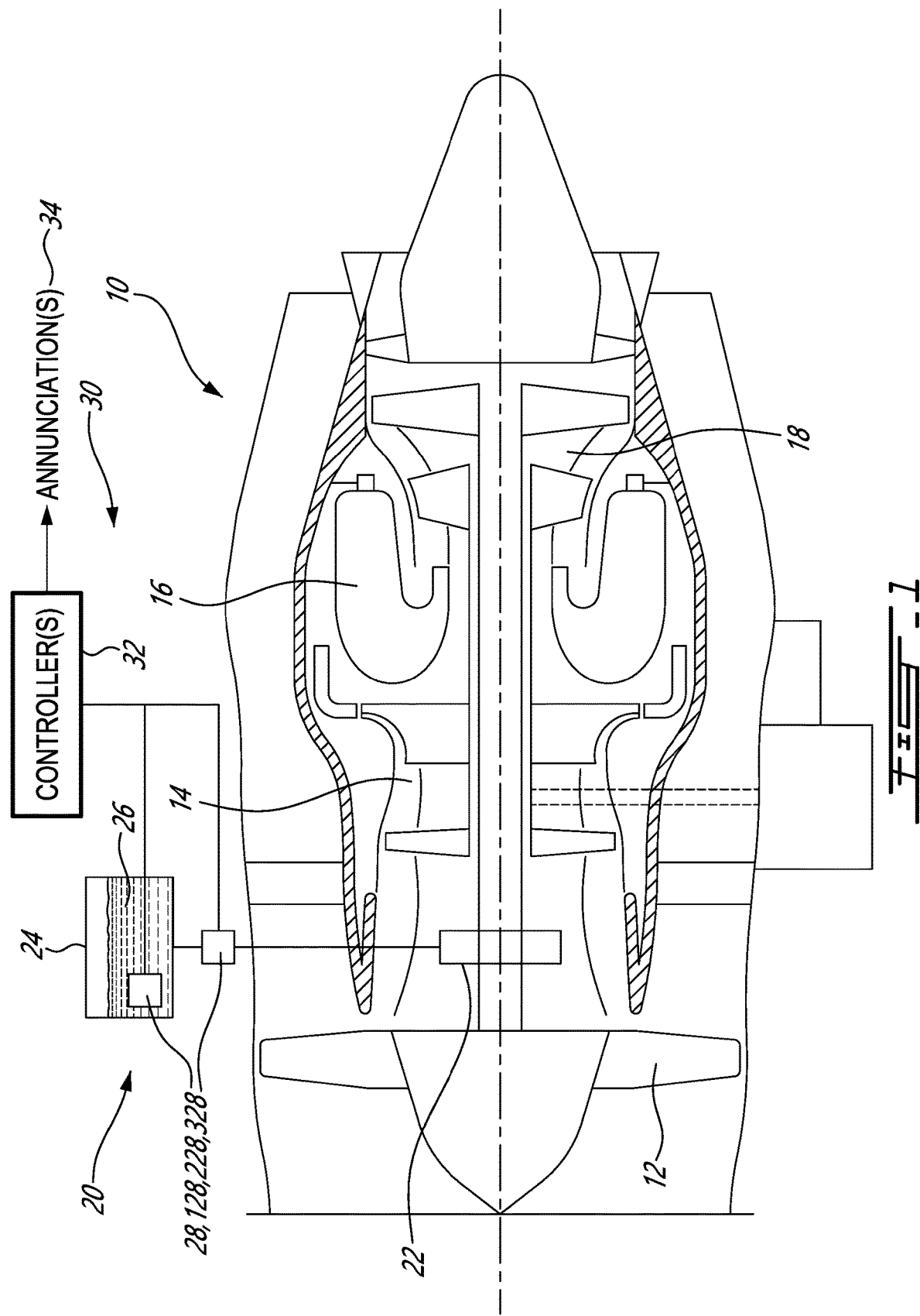

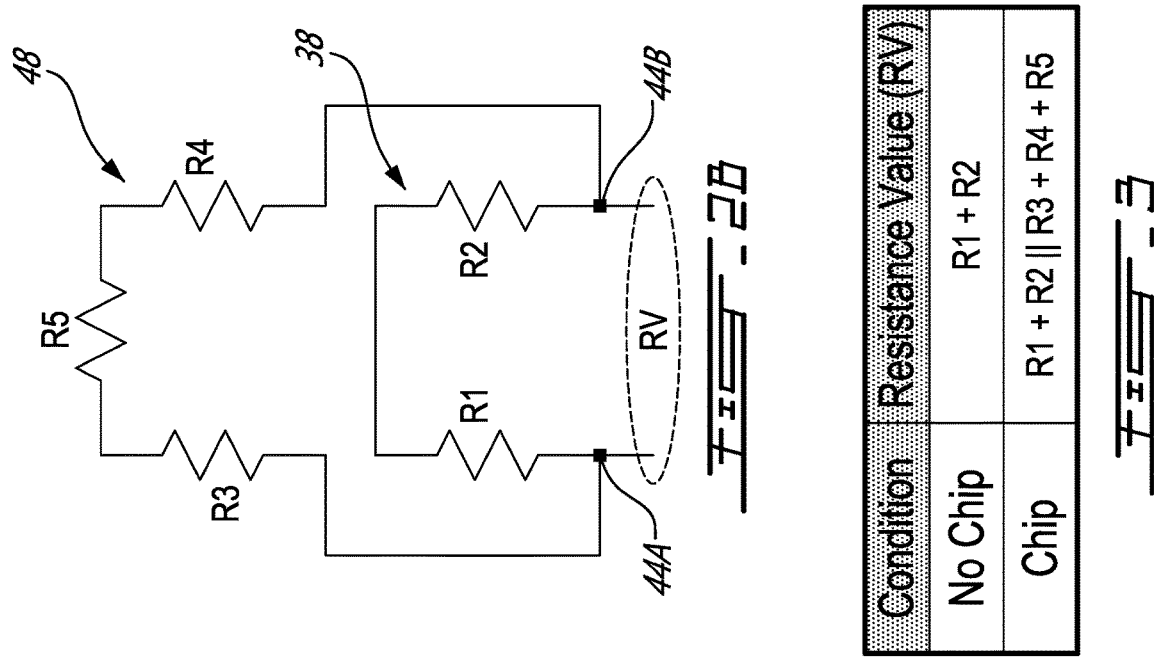
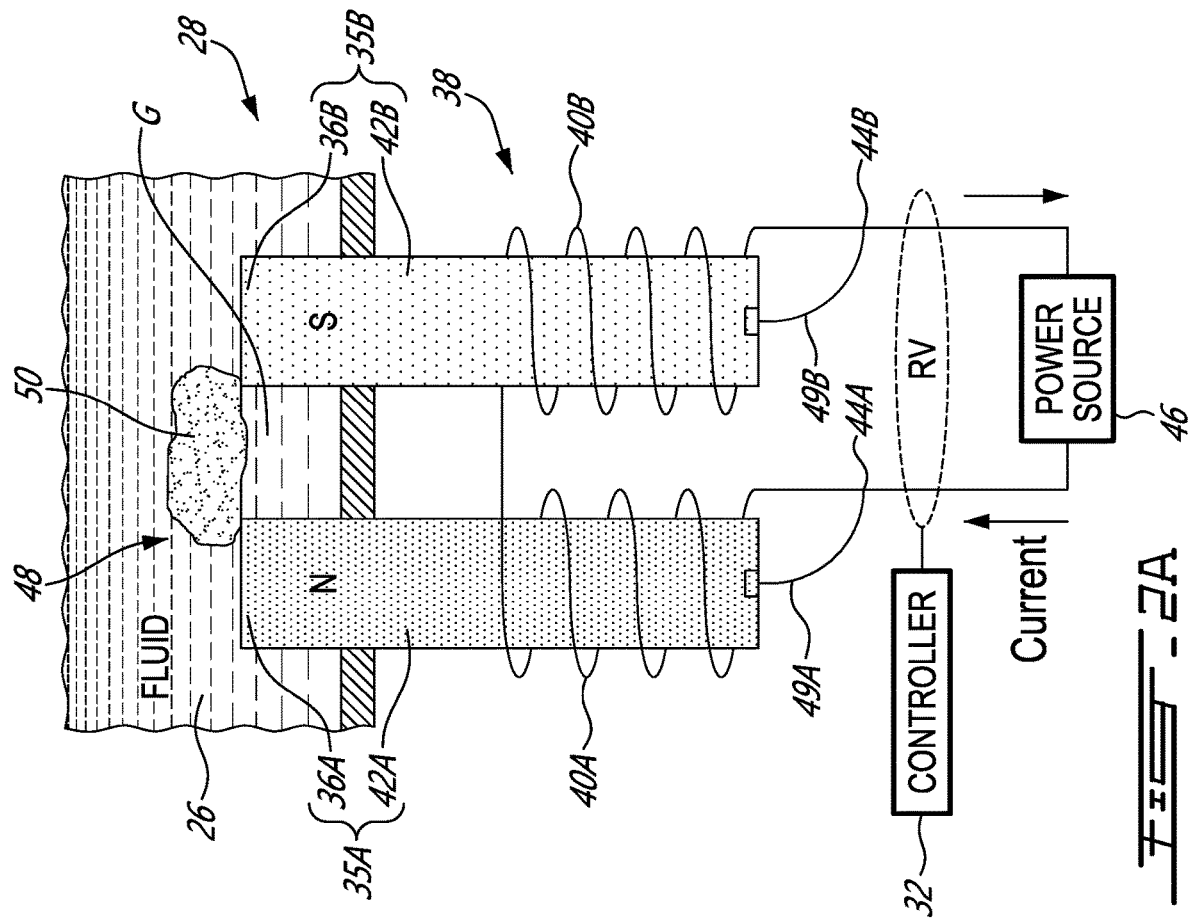

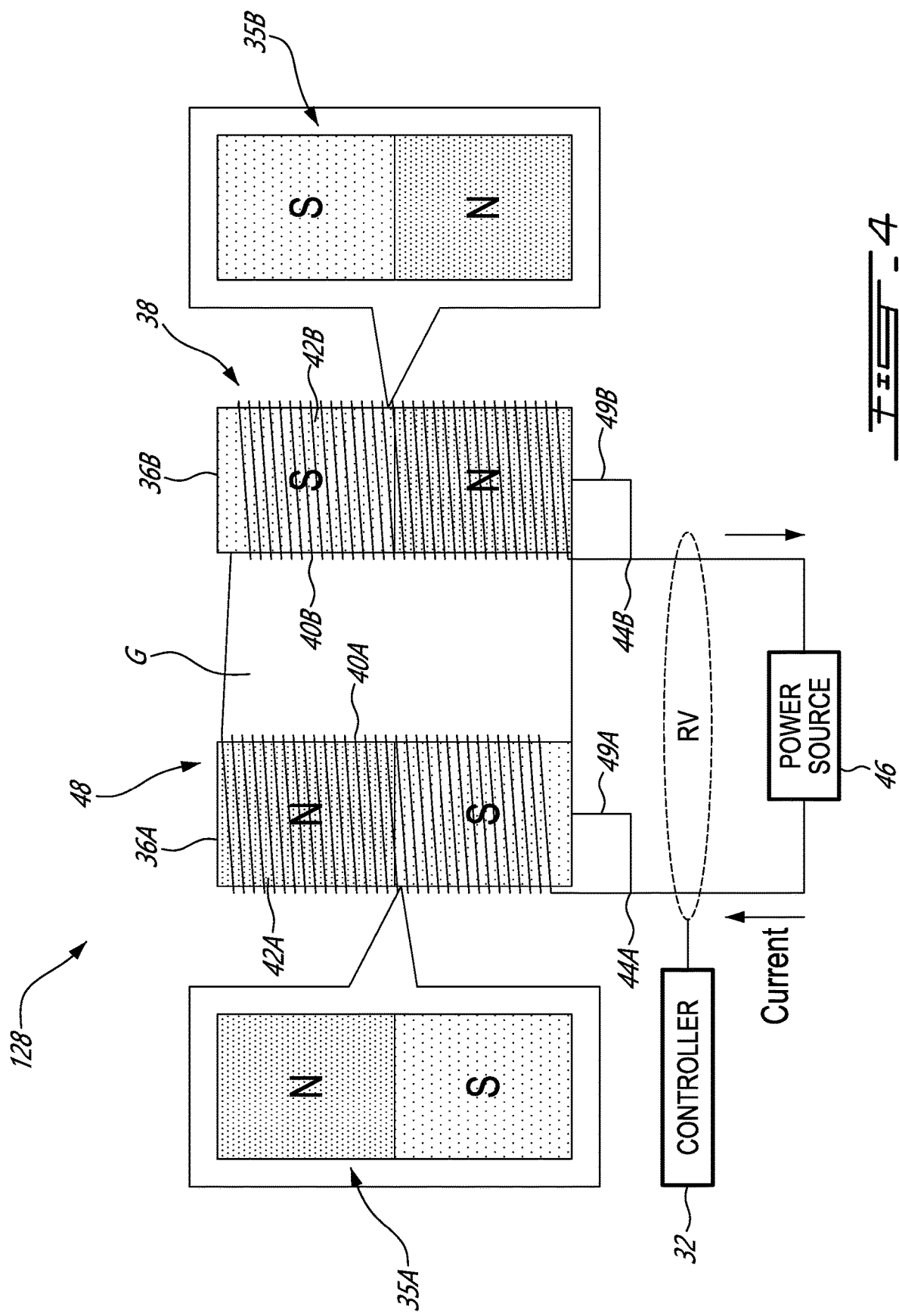

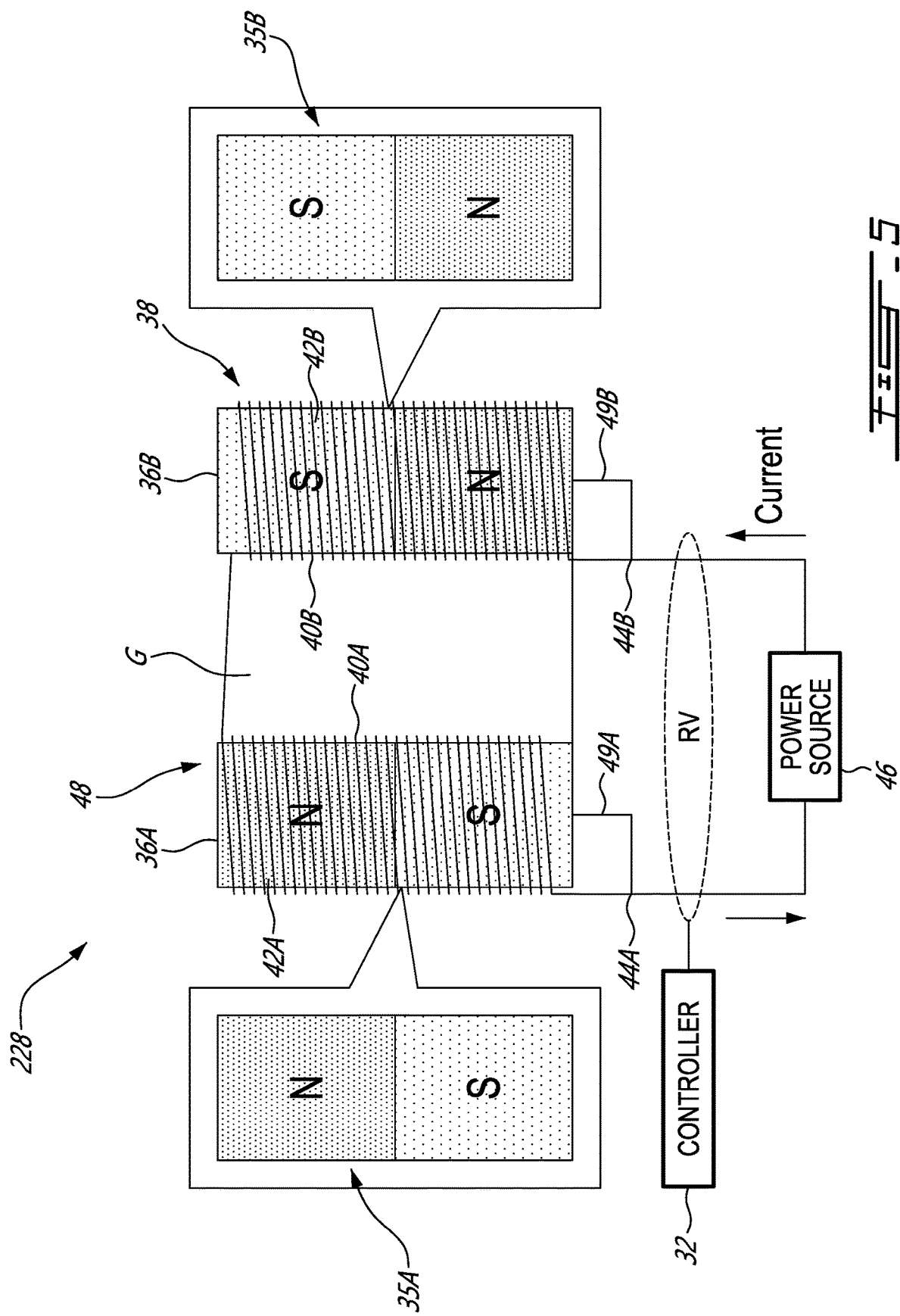

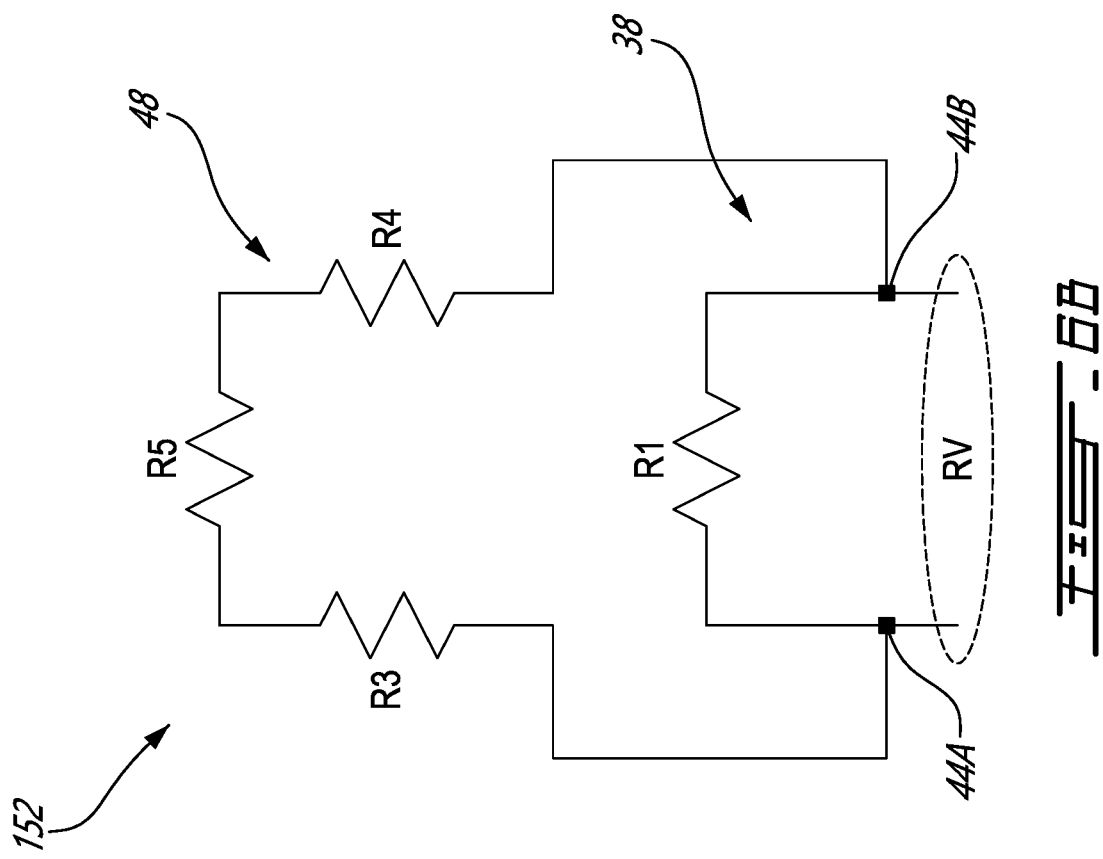

ELECTROMAGNETIC CHIP DETECTOR

TECHNICAL FIELD

The disclosure relates generally to health monitoring of engines, and more particularly to detecting chips in fluids of aircraft engines.

BACKGROUND

A magnetic chip detector in a lubrication system of an aircraft engine can detect the presence of metallic chips in the lubricating fluid. The chip detector is immersed in the lubricating fluid so as to be exposed to the chips carried by the lubricating fluid. The presence of chips in the lubricating fluid may indicate a developing and/or impending mechanical problem exhibiting excessive wear of one or more components of the aircraft engine interacting with the lubrication system. When chips are collected by the chip detector, a gap between two electric terminals is eventually bridged so as to provide electric continuity and cause an indication (e.g., alarm) to be provided to an operator of the aircraft so that an appropriate action can be taken if necessary. The presence of metallic chips in engine fluid can be indicative of a deteriorating engine health condition and it is desirable to improve chip detection in aircraft engines.

SUMMARY

In one aspect, the disclosure describes an electromagnetic chip detector for detecting a metallic chip in lubricating fluid of an engine. The electromagnetic chip detector comprises:
  a first electrically conductive terminal;
  a second electrically conductive terminal spaced apart from the first electrically conductive terminal to define a chip-receiving gap therebetween;
  a magnetizing circuit including:
    a first coil inductively coupled to the first electrically conductive terminal to generate a first generated magnetic field of a first polarity; and
    a second coil inductively coupled to the second electrically conductive terminal to generate a second generated magnetic field of a second polarity opposite the first polarity, the first coil and the second coil being electrically connected in series between a first node and a second node;
  a chip detection circuit in parallel with the magnetizing circuit, the chip detection circuit including:
    the first electrically conductive terminal electrically connected to the first node;
    the second electrically conductive terminal electrically connected to the second node; and
    the chip-receiving gap defined between the first electrically conductive terminal and the second electrically conductive terminal.

In another aspect, the disclosure describes an electromagnetic chip detector for detecting a metallic chip in engine fluid of an engine. The electromagnetic chip detector comprises:
  a first electrically conductive terminal;
  a second electrically conductive terminal spaced apart from the first electrically conductive terminal to define a chip-receiving gap therebetween;
  a first circuit magnetizing the first electrically conductive terminal to have a first polarity and magnetizing the second electrically conductive terminal to have a second polarity opposite the first polarity;
  a second circuit detecting a presence of a chip electrically connecting the first electrically conductive terminal and the second electrically conductive terminal together; and
  a power source supplying electric current to both the first circuit and the second circuit via a first node and a second node when the chip electrically connects the first electrically conductive terminal to the second electrically conductive terminal.

In a further aspect, the disclosure describes a method of detecting a metallic chip in engine fluid of an engine using an electromagnetic chip detector. The method comprises:
  supplying an electric current to a circuit extending between a first node and a second node to magnetize both a first electrically conductive terminal and a second electrically conductive terminal spaced apart from each other to define a chip-receiving gap therebetween; and
  detecting a change in resistance across the first node and the second node, the change in resistance being indicative of a capture of the metallic chip by the electromagnetic chip detector, the metallic chip electrically connecting the first electrically conductive terminal to the second electrically conductive terminal, the first electrically conductive terminal being electrically connected to the first node, and the second electrically conductive terminal being electrically connected to the second node.

Further details of these and other aspects of the subject matter of this application will be apparent from the detailed description included below and the drawings.

DESCRIPTION OF THE DRAWINGS

Reference is now made to the accompanying drawings, in which:

FIG. 1 is a schematic axial cross-section view of a turbofan gas turbine engine including an electromagnetic chip detector as described herein;

FIG. 2A is a schematic representation of an exemplary electromagnetic chip detector;

FIG. 2B is an electric circuit diagram associated with the electromagnetic chip detector of FIG. 2A;

FIG. 3 is a table of measurable resistance values associated with no chip being captured by the electromagnetic chip detector, and one or more chips being captured by the electromagnetic chip detector;

FIG. 4 is a schematic illustration of another exemplary electromagnetic chip detector;

FIG. 5 is a schematic illustration of another exemplary electromagnetic chip detector;

FIG. 6B is an electric circuit diagram associated with the electromagnetic chip detector of FIG. 6A;

FIG. 7 is a table of measurable resistance values associated with no chip being captured by the electromagnetic chip detector of FIGS. 6A and 6B, and one or more chips being captured by the electromagnetic chip detector of FIGS. 6A and 6B.

DETAILED DESCRIPTION

Figure 6A:
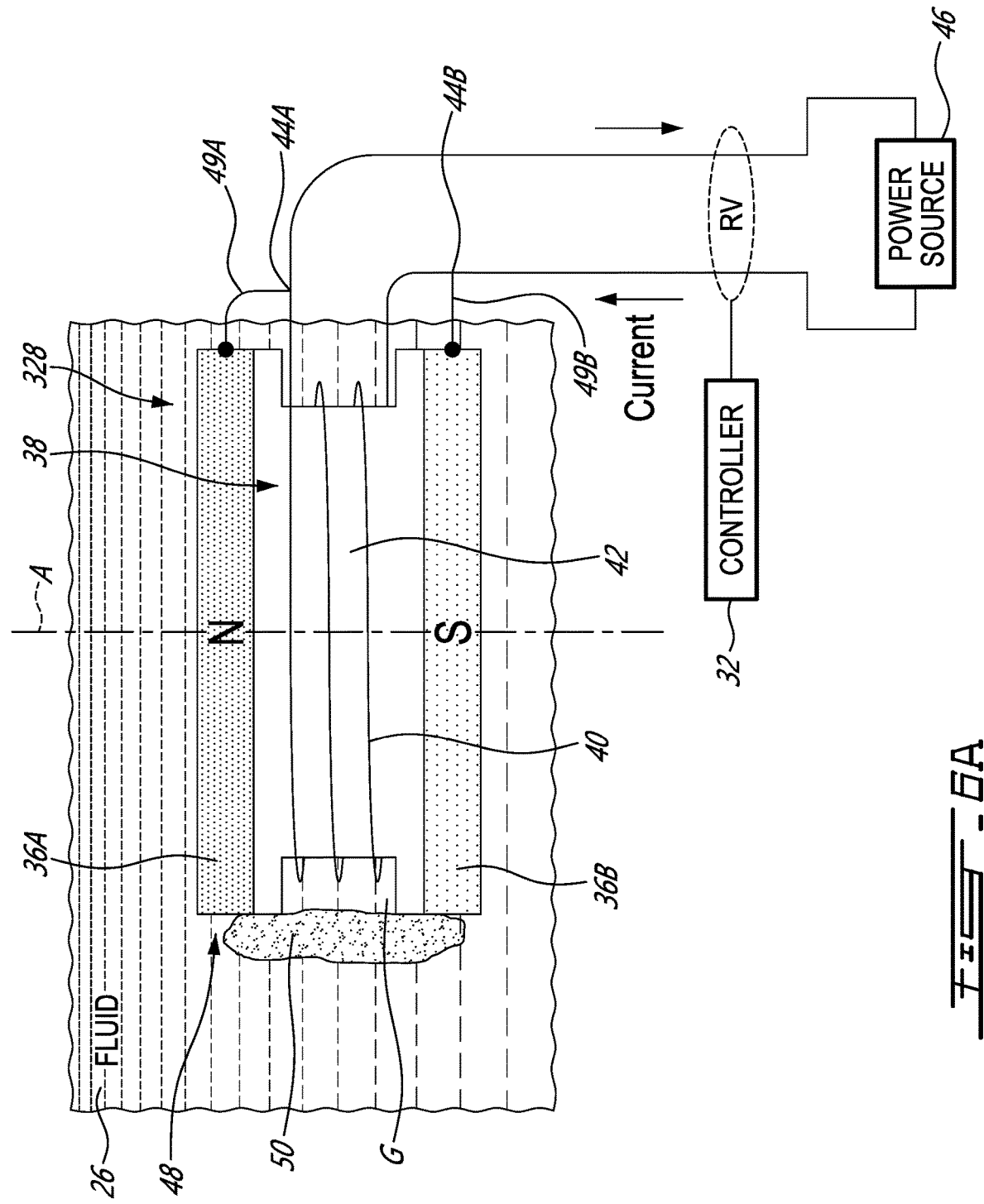
FIG. 6A is a schematic representation of another exemplary electromagnetic chip detector.

This disclosure relates to detectors and methods for detecting metallic chips (e.g., particles, slivers, shavings, debris) in engine (e.g., lubricating, cooling) fluids. In some embodiments, the detectors and methods described herein make use of electromagnets that provide a relatively consistent and more precisely set magnetic strength as opposed to relying only on permanent (e.g., manufactured or rare earth) magnets that can be fragile and susceptible to demagnetization (i.e., lose their magnetic strength) over time. The use of the detectors described herein may, in some embodiments, reduce the need for periodic maintenance actions to verify the magnetic strength of the terminals (e.g., prongs, disks) of the detectors. The use of electromagnetism to tailor a desired magnetic strength may facilitate the design and customization of the detectors for various applications. In some embodiments, the detectors described herein may provide both electro-magnetization and chip detection functionalities via two nodes (e.g., junctions, two-pin interface) to facilitate the integration and interfacing of the detectors with (e.g., aircraft) engine designs, and retrofitting the detectors into existing engine installations.

In some embodiments, the detectors and methods described herein may be configured to use electromagnetism to produce the magnetic strength and also change the magnetic strength of the terminals of the detectors after the capture of one or more metallic chips. For example, the detectors may be configured so that a first magnetic strength used to attract one or more chips is different from a second magnetic strength used to retain/hold the one or more chips after the chip(s) has/have been captured. In some embodiments, the chip detectors described herein may also function as chip collectors. In various embodiments, the detectors may use electromagnetism in combination with terminals that are (or are magnetized by) permanent magnets or with terminals that are not (or are not magnetized by) permanent magnets.

Aspects of various embodiments are described herein through reference to the drawings. Even though the description below is provided in relation to lubricating fluid, it is understood that some embodiments of the chip detectors, systems and methods described herein may also be used with other types of engine fluids such as engine coolant for example.

The term "connected" may include both direct connection (in which two elements contact each other) and indirect connection (in which at least one additional element is located between the two elements).

The term "substantially" as used herein may be applied to modify any quantitative representation which could permissibly vary without resulting in a change in the basic function to which it is related.

FIG. 1 is a schematic axial cross-section view of turbofan aircraft engine 10 (referred hereinafter as "engine 10") preferably provided for use in subsonic flight, generally comprising, in serial flow communication, fan 12 through which ambient air is propelled, multistage compressor 14 for pressurizing the air, combustor 16 in which the compressed air is mixed with fuel and ignited for generating an annular stream of hot combustion gases, and turbine section 18 for extracting energy from the combustion gases. Engine 10 may be mounted to an aircraft and used to propel such aircraft. Even though FIG. 1 shows engine 10 being of the turbofan type, it is understood that aspects of the present disclosure are also applicable to other (e.g., turboshaft, turboprop, internal combustion) types of aircraft engines.

Engine 10 may include lubrication (and/or other fluid) system 20 shown schematically and partially in FIG. 1. Lubrication system 20 may serve to lubricate, cool and clean one or more lubrication loads 22 such as bearings and gears of engine 10. Lubrication system 20 may include tank 24 and other components such as one or more pumps, one or more valves, and one or more filters. Tank 24 may be a reservoir containing a supply of lubricating fluid 26 such as oil for use by lubrication system 20. Lubrication system 20 may include one or more electromagnetic chip detectors 28. For example, lubrication system 20 may include a single chip detector 28 or a plurality of chip detectors 28 disposed at different locations within lubrication system 20. Chip detector 28 may be in contact with (e.g., partially immersed in) lubricating fluid 26 during operation. For example, chip detector 28 be disposed inside tank 24, inside a gearbox, or in a scavenge line.

Chip detector 28 may be part of chip detection system 30 (referred hereinafter as "system 30") and may be associated with and/or may be part of engine 10. System 30 may include controller 32 or other detection circuitry operatively connected to chip detector 28. In various embodiments, controller 32 may include or form part of a Full Authority Digital Engine Control (FADEC) which may, for example, include one or more digital computer(s) or other data processors, sometimes referred to as electronic engine controller(s) (EEC) and related accessories that control at least some aspect(s) of performance of engine 10. Controller 32 may, for example, be configured to make decisions regarding the operation of engine 10. Controller 32 may include one or more data processors and non-transitory machine-readable memory. Various aspects of the present disclosure may be embodied as systems, devices, methods and/or computer program products.

Controller 32 may receive input(s) from chip detector 28, perform one or more procedures or steps defined by instructions stored in the memory to generate output(s) such as triggering a suitable annunciation 34 when a chip is captured by chip detector 28 for example. Controller 32 may initiate annunciation 34 which may alert a pilot of the aircraft and/or another interested party. Annunciation 34 may be visual (e.g., indicator light or message) or aural (e.g., tone or spoken message). It is understood that in some embodiments, controller 32 may be replaced by suitable analog circuitry that causes annunciation 34 upon the detection of the chip.

Once the chip detection is triggered by one or more chips being captured by chip detector 28, the pilot may be required to return to the ground (e.g., base, airport) as soon as possible, and remove (or have maintenance personnel remove) chip detector 28 for visual inspection. The visual inspection verifies whether significant debris has been collected by chip detector 28 and hence whether maintenance is required before the aircraft can be dispatched again.

FIG. 2A is an exemplary schematic representation of chip detector 28. Chip detector 28 may be a prong-type magnetic chip detector where magnetization is provided partially or wholly by way of electro-magnetization. Chip detector 28 may include first prong 35A defining first electrically conductive terminal 36A (referred hereinafter as "first terminal 36A"), and second prong 35B defining second electrically conductive terminal 36B (referred hereinafter as "second terminal 36B"). First terminal 36A and second terminal 36B may be spaced apart from each other to define chip-receiving gap G therebetween. The size(s) of gap G (i.e., the spacing between first terminal 36A and second terminal 36B) may be selected based on the chip sizes of interest. In some embodiments, the size of gap G may be between 1/64" (0.4 mm) and 1/8" (3.2 mm) for example.

Chip detector 28 may include magnetizing circuit 38 for magnetizing both first terminal 36A and second terminal 36B. Magnetizing circuit 38 may include first coil 40A inductively coupled to first terminal 36A to generate a first generated magnetic field of a first polarity. For example, first coil 40A may be wound around first magnetic core 42A of first prong 35A so that the first generated magnetic field may cause first terminal 36A to have a north (N) polarity. First coil 40A may be electrically isolated from first terminal 36A via a suitable electric insulator. Second coil 40B may be inductively coupled to second terminal 36B to generate a second generated magnetic field of a second polarity opposite the first polarity. For example, second coil 40B may be wound around second magnetic core 42B of second prong 35B so that the second generated magnetic field may cause second terminal 36B to have a south (S) polarity. Second coil 40B may be electrically isolated from second terminal 36B via a suitable electric insulator. The opposite polarities of first terminal 36A and second terminal 36B may be achieved by having first coil 40A and second coil 40B wound in opposite directions around first magnetic core 42A and second magnetic core 42B respectively.

First coil 40A and second coil 40B may be electrically connected together in series and extend between first node 44A and second node 44B. An electric (e.g., direct) current supplied to first coil 40A and second coil 40B may cause the magnetization of first terminal 36A and second terminal 36B in opposite polarities. The electric current may be supplied by power source 46, which may include a battery or a direct current (DC) power bus of engine 10 or of an aircraft to which engine 10 may be mounted. In various embodiments, the electric current used for magnetization may be delivered to magnetizing circuit 38 via controller 32 or separately of controller 32. The electric current used for magnetization may be supplied to both first coil 40A and second coil 40B via first node 44A and second node 44B due to the series connection between first coil 40A and second coil 40B.

Chip detector 28 may include chip detection circuit 48 that is arranged in parallel with magnetizing circuit 38. Chip detection circuit 48 may serve to detect a presence of one or more chips 50 electrically connecting first terminal 36A and second terminal 36B. Chip detection circuit 48 may include first terminal 36A electrically connected to first node 44A via first conductor 49A for example. Chip detection circuit 48 may include second terminal 36B electrically connected to second node 44B via second conductor 49B for example. Chip detection circuit 48 may also include gap G defined between first terminal 36A and second terminal 36B. In other words, chip detection circuit 48 may include first terminal 36A, gap G and second terminal 36B arranged in series, and extending between the same first node 44A and second node 44B between which first coil 40A and second coil 40B are disposed.

First node 44A and second node 44B may define two connections (i.e., one supply and one return) that may be used to interface with both magnetizing circuit 38 and with chip-detection circuit 48. In some embodiments, no additional connections may be required to interface with chip detector 28 so that a 2-pin connector may be used to interface controller 32 with chip detector 28 for example.

In various embodiments, first prong 35A and second prong 35B may or may not be permanent magnets. However, first prong 35A and second prong 35B may be made of a material that is susceptible to be magnetized via magnetization circuit 38. In some embodiments, first prong 35A may be substantially non-magnetized in an absence of the first magnetic field generated via first coil 40A. In some embodiments, second prong 35B may be substantially non-magnetized in an absence of the second magnetic field generated via second coil 40B. In other words, first prong 35A and second prong 35B may be made of a non-magnetized material such as a ferromagnetic or ferrimagnetic material such as iron for example. First magnetic core 42A and second magnetic core 42B may concentrate the magnetic flux produced by first coil 40A and second coil 40B respectively.

In some embodiments, first prong 35A and second prong 35B may be of cylindrical or other suitable shape. In some embodiments, gap G may be filled with an electrically-isolating material to leave the end faces of first terminal 36A and of second terminal 36B exposed to lubricating fluid 26. Such configuration of chip detector 28 may facilitate cleaning and promote durability of chip detector 28.

During operation of chip detector 28 when first terminal 36A and second terminal 36B of chip detector 28 are immersed in lubricating fluid 26, the opposite polarities of first terminal 36A and second terminal 36B may cause one or more metallic chips 50 that are present in lubricating fluid 26 to be magnetically drawn toward gap G between first terminal 36A and second terminal 36B. Chips 50 that are carried by lubricating fluid 26 may be from metallic engine parts such as gear teeth or bearings for example. When chip 50 of a sufficient size, or a plurality of chips 50, is/are attracted to and collected by chip detector 28, chip(s) 50 may electrically bridge (e.g., short-circuit) gap G defined between first terminal 36A and second terminal 36B to complete chip detection circuit 48 that includes gap G. As explained further below, controller 32 or other annunciation circuitry connected to chip detector 28 may detect the capture of chip(s) 50 by way of a change in resistance value RV measured across first node 44A and second node 44B. Upon detection of such change in resistance value RV, controller 32 may cause annunciation 34 (shown in FIG. 1) to be generated.

When no chips 50 electrically connect first terminal 36A to second terminal 36B, power source 46 may supply electric current to magnetizing circuit 38 via first node 44A and second node 44B but not to chip detection circuit 48. However, when one or more chips 50 electrically connect first terminal 36A to second terminal 36B, power source 46 may supply electric current to both magnetizing circuit 38 and to chip detection circuit 48 via first node 44A and second node 44B. In case of the electric power delivered to magnetizing circuit 38 and chip detection circuit 48 being of constant voltage for example, the completion of chip detection circuit 48 by chip(s) 50 may cause some current to be delivered to chip detection circuit 48 and this may result in a decrease in current being delivered to magnetizing circuit 38. In various embodiments, such decrease in current to magnetizing circuit 38 may cause a change in magnetic strength associated with first terminal 36A and second terminal 36B. In other words, when one or more chips 50 are captured by chip detector 28, the closing of chip detection circuit 48 by chip(s) 50 may cause a decrease in current passing through magnetizing circuit 38 so that a magnetization of first terminal 36A and of second terminal 36B may be altered. In some embodiments where first terminal 36A and second terminal 36B are not permanent magnets, such change in magnetic strength may be a decrease in magnetic strength associated with the capture of chip(s) 50. In embodiments where first terminal 36A and second terminal 36B are permanent magnets, such change in magnetic strength may be a decrease or an increase in magnetic strength associated with the capture of chip(s) 50 as explained in relation to FIGS. 4 and 5 below.

Chip detector 28 may include elements (e.g., resistor(s), coils/inductors) additional to those shown herein. For example, elements of magnetizing circuit 38 and of chip detection circuit 48 may be selected (e.g., suitably balanced) such that once the chip detection circuit 48 is closed by chip(s) 50, magnetizing circuit 38 will continue to receive sufficient current flow from power source 46 to produce enough magnetic strength to hold the captured chip(s) 50. Balancing (i.e., proportioning) the resistances of magnetizing circuit 38 and of chip detection circuit 48 may be achieved in a number of ways. For example, the resistance of chip detection circuit 48 can be adjusted by way of one or more coils similar to those of magnetizing circuit 38. The respective resistances of chip detection circuit 48 and of magnetizing circuit 38 may be adjusted by selecting a desired number of turns in each coil. The respective resistances of chip detection circuit 48 and of magnetizing circuit 38 may also be adjusted by selecting desired wire diameters and lengths in each circuit. The respective resistances of chip detection circuit 48 and of magnetizing circuit 38 may also be adjusted by the addition of one or more resistors. Any suitable combination of the above approaches may be used to adjust the respective resistances of chip detection circuit 48 and of magnetizing circuit 38.

In some embodiments, two or more chip detectors 28 may be combined or integrated together in a single package to define a multi-zone chip detector. Such multi-zone chip detector may be used to detect multiple chips 50 and used to define a legitimate chip detection only when a minimum number of chips 50 have been detected for example.

FIG. 2B is an equivalent electric circuit diagram 52 associated with chip detector 28 of FIG. 2A. In reference to magnetizing circuit 38 shown in diagram 52, first coil 40A may be represented by equivalent resistance R1, and second coil 40B may be represented by equivalent resistance R2 where resistances R1 and R2 may be connected in series between first node 44A and second node 44B. In reference to chip detection circuit 48, first prong 35A may be represented by equivalent resistance R3. Second prong 35B may be represented by equivalent resistance R4. The one or more chips 50 captured by chip detector 28 and bridging gap G may be represented by equivalent resistance R5. Resistances R3, R4 and R5 may be connected in series between first node 44A and second node 44B.

FIG. 3 is a table of measurable resistance values RV associated with no chip being captured by chip detector 28, and with one or more chips 50 being captured by chip detector 28 and bridging gap G. For example, when no chip is captured by chip detector 28, chip detection circuit 48 may have an open-circuit state due to the absence of resistance R5 in FIG. 2B, and magnetizing circuit 38 may provide a first known resistance (e.g., RV=R1+R2) across first node 44A and second node 44B that may be read by an interrogating circuit such as controller 32. On the other hand, when one or more chips 50 are captured by chip detector 28 and electrically bridge gap G, chip detection circuit 48 may be closed due to the presence of resistance R5 in FIG. 2B. In this situation, the combination of magnetizing circuit 38 and of chip detection circuit 48 arranged in parallel may provide a second resistance (e.g., RV=R1+R2∥R3+R4+R5) across first node 44A and second node 44B that may be read by the interrogating circuit such as controller 32. Such change in resistance value RV measured across first node 44A and second node 44B may be interpreted by controller 32 as a legitimate capture of one or more chips 50 and may cause annunciation 34 to be generated.

FIG. 4 is a schematic illustration of another exemplary electromagnetic chip detector 128 that may be used in system 30. Chip detector 128 may have elements of chip detector 28 described above, and like elements are identified using like reference numerals. Chip detector 128 may also be configured according to circuit diagram 52 of FIG. 2B. As illustrated in callouts shown in FIG. 4, first prong 35A and second prong 35B may be permanent magnets having opposite orientations so that first terminal 36A and second terminal 36B have opposite polarities. Such permanent magnets may each have their own persistent magnetic field and retain their magnetism after being removed from an external magnetic field. In various embodiments, the permanent magnets may be rare earth (e.g., neodymium or and samarium-cobalt) magnets, ferrite or alnico magnets.

In addition to being permanent magnets, first prong 35A and second prong 35B may also be susceptible to magnetization by electromagnetism. Accordingly, first coil 40A may be inductively coupled to first terminal 36A, and second coil 40B may be inductively coupled to second terminal 36B. The winding direction of first coil 40A around first prong 35A and the direction of current flow through magnetizing circuit 38 may be arranged so that the first magnetic field generated by first coil 40A may have the same polarity as and therefore supplement (i.e., be additive to) the persistent (i.e., intrinsic) magnetic field of first prong 35A. Similarly, the winding direction of second coil 40B around second prong 35B and the direction of current flow through magnetizing circuit 38 may be arranged so that the second magnetic field generated by second coil 40B may have the same polarity as and therefore supplement (i.e., be additive to) the persistent (i.e., intrinsic) magnetic field of second prong 35B.

During operation, when no chips 50 are captured by chip detector 128, the magnetic strength of chip detector 128 provided by the permanent magnets of first prong 35A and second prong 35B may be supplemented by magnetizing circuit 38. When one or more chips 50 are captured by chip detector 128, the closing of chip detection circuit 48 by chip(s) 50 may cause a decrease in current passing through magnetizing circuit 38. Such decrease in current may cause the contribution of the magnetization of the first terminal 36A and of second terminal 36B from magnetization circuit 38 to be decreased after the capture of chip(s) 50 by chip detector 128. The resulting decreased magnetization may be selected to be sufficiently high to retain the captured chip(s) 50.

FIG. 5 is a schematic illustration of another exemplary electromagnetic chip detector 228 that may be used in system 30. Chip detector 228 may have elements of chip detectors 28, 128 described above, and like elements are identified using like reference numerals. Chip detector 228 may also be configured according to circuit diagram 52 of FIG. 2B. As illustrated in callouts shown in FIG. 5, first prong 35A and second prong 35B may be permanent magnets having opposite orientations so that first terminal 36A and second terminal 36B have opposite polarities. Such permanent magnets may each have their own persistent magnetic field and retain their magnetism after being removed from an external magnetic field. In addition to being permanent magnets, first prong 35A and second prong 35B may also be susceptible to magnetization by electromagnetism. Accordingly, first coil 40A may be inductively coupled to first terminal 36A, and second coil 40B may be inductively coupled to second terminal 36B.

In contrast with chip detector 128, the winding direction of first coil 40A around first prong 35A and the direction of current flow through magnetizing circuit 38 may be arranged so that the first magnetic field generated by first coil 40A may have the opposite polarity as and may therefore oppose (i.e., be subtractive from) the persistent (i.e., intrinsic) magnetic field of first prong 35A. Similarly, the winding direction of second coil 40B around second prong 35B and the direction of current flow through magnetizing circuit 38 may be arranged so that the second magnetic field generated by second coil 40B may have the opposite polarity as and may therefore oppose (i.e., be subtractive from) the persistent (i.e., intrinsic) magnetic field of second prong 35B.

During operation, when no chips 50 are captured by chip detector 228, the magnetic strength of chip detector 228 provided by the permanent magnets of first prong 35A and second prong 35B may be decreased by magnetizing circuit 38. When one or more chips 50 are captured by chip detector 228, the closing of chip detection circuit 48 by chip(s) 50 may cause a decrease in current passing through magnetizing circuit 38. Such decrease in current may cause the opposing magnetization of the first terminal 36A and of second terminal 36B by magnetizing circuit 38 to be decreased after the capture of chip(s) 50 by chip detector 228. This decrease in opposing magnetization may in turn cause the overall magnetic strength of chip detector 228 to be increased due to the persistent magnetic field of the permanent magnets. In other words, the capture of chip(s) 50 may cause an increase in magnetic strength for retaining the captured chip(s) by chip detector 228.

FIG. 6A is a schematic representation of another exemplary electromagnetic chip detector 328 that may be used in system 30. Chip detector 328 may have elements of chip detectors 28, 128, 228 described above, and like elements are identified using like reference numerals. Chip detector 328 may be an axial disk-type chip detector. Chip detector 328 may include magnetic core 42 extending and retained between first terminal 36A and second terminal 36B. Suitable electrically non-conductive and non-magnetically permeable isolators (not shown) may be disposed between magnetic core 42 and the respective first terminal 36A and second terminal 36B. First terminal 36A and second terminal 36B may be metallic (e.g., steel) end caps between which magnetic core 42 is retained. First terminal 36A and second terminal 36B may be spaced apart from each other to define chip-receiving gap G therebetween to receive one or more chips 50. In some embodiments, magnetic core 42, first terminal 36A and second terminal 36B may be disk-shaped and may be disposed in a coaxial manner along axis A. First terminal 36A and second terminal 36B may be immersed into and in contact with lubricating fluid 26. In various embodiments, gap G may extend partially or substantially entirely around axis A.

Chip detector 328 may include magnetizing circuit 38 for magnetizing both first terminal 36A and second terminal 36B. Magnetizing circuit 38 may include coil 40 wound around and inductively coupled to magnetic core 42 to generate a magnetic field causing first terminal 36A to have a north (N) polarity and second terminal 36B to have a south (S) polarity. Coil 40 may be electrically isolated from magnetic core 42 via a suitable electric insulator. Coil 40 may be electrically connected to and extend between first node 44A and second node 44B. An electric (e.g., direct) current supplied to coil 40 may cause the magnetization of first terminal 36A and of second terminal 36B in opposite polarities. The electric current may be supplied by power source 46 via controller 32 or separately of controller 32.

Chip detector 328 may include chip detection circuit 48 that is arranged in parallel with magnetizing circuit 38. Chip detection circuit 48 may serve to detect a presence of one or more chips 50 electrically connecting first terminal 36A and second terminal 36B together. Chip detection circuit 48 may include first terminal 36A electrically connected to first node 44A via first conductor 49A for example. Chip detection circuit 48 may include second terminal 36B electrically connected to second node 44B via second conductor 49B for example. Chip detection circuit 48 may also include gap G defined between first terminal 36A and second terminal 36B. In other words, chip detection circuit 48 may include first terminal 36A, gap G and second terminal 36B arranged in series, and extending between the same first node 44A and second node 44B between which coil 40 is disposed.

First node 44A and second node 44B may define two connections (i.e., one supply and one return) that may be used to interface with both magnetizing circuit 38 and with chip-detection circuit 48. In some embodiments, no additional connections may be required to interface with chip detector 328 so that a 2-pin connector may be used to interface controller 32 with chip detector 328 for example.

In various embodiments, magnetic core 42 may or may not be a permanent magnet. However, magnetic core 42 may be made of a material that is suitable for concentrating magnetic flux generated using coil 40. In some embodiments, magnetic core 42 may be made of a non-magnetized material. In some embodiments, magnetic core 42 may be a permanent magnet producing a persistent magnetic field. Similarly to chip detectors 128 and 228 shown in FIGS. 4 and 5, the magnetic field generated using coil 40 and the persistent magnetic field of the permanent magnet may be arranged in an additive or subtractive manner. For example, in various embodiments, the magnetic field generated using coil 40 may supplement or oppose the persistent magnetic field of the permanent magnet to achieve either a decrease or an increase in magnetic strength of detector 328 after the capture of chip(s) 50.

During operation of chip detector 328 when first terminal 36A and second terminal 36B of chip detector 328 are immersed in lubricating fluid 26, the opposite polarities of first terminal 36A and second terminal 36B may cause one or more metallic chips 50 that are present in lubricating fluid 26 to be magnetically drawn toward gap G between first terminal 36A and second terminal 36B. When chip 50 of a sufficient size, or a plurality of chips 50, is/are attracted to chip detector 328, chip(s) 50 may electrically bridge (e.g., short-circuit) gap G defined between first terminal 36A and second terminal 36B to complete chip detection circuit 48 that includes gap G. Controller 32 or other annunciation circuitry connected to chip detector 328 may detect the capture of chip(s) 50 by way of a change in resistance value RV measured across first node 44A and second node 44B. Upon detection of such change in resistance value RV, controller 32 may cause annunciation 34 (shown in FIG. 1) to be generated. Chip detector 328 may include elements (e.g., resistor(s), coils/inductors) additional to those shown herein to adjust the respective resistances of chip detection circuit 48 and of magnetizing circuit 38 to achieve a suitable resistance proportion between magnetizing circuit 38 and chip detection circuit 48 as explained above.

When no chips 50 electrically connect first terminal 36A to second terminal 36B, power source 46 may supply electric current to magnetizing circuit 38 via first node 44A and second node 44B but not to chip detection circuit 48. However, when one or more chips 50 electrically connect first terminal 36A to second terminal 36B, power source 46 may supply electric current to both magnetizing circuit 38 and to chip detection circuit 48 via first node 44A and second node 44B.

FIG. 6B is an equivalent electric circuit diagram 152 associated with chip detector 328 of FIG. 6A. In contrast with diagram 52 of FIG. 2B, diagram 152 may not include resistance R2 since only one coil 40 is required to magnetize both first terminal 36A and second terminal 36B with opposite polarities. In reference to magnetizing circuit 38, coil 40 may be represented by equivalent resistance R1 disposed between first node 44A and second node 44B. In reference to chip detection circuit 48, first terminal 36A may be represented by equivalent resistance R3. Second terminal 36B may be represented by equivalent resistance R4. The one or more chips 50 captured by chip detector 328 and bridging gap G may be represented by equivalent resistance R5. Resistances R3, R4 and R5 may be connected in series between first node 44A and second node 44B. Resistances R3, R4 and R5 may be connected in parallel with resistance R1.

FIG. 7 is a table of measurable resistance values RV associated with no chip being captured by chip detector 328, and with one or more chips 50 being captured by chip detector 328 and bridging gap G. For example, when no chip is captured by chip detector 328, chip detection circuit 48 may have an open-circuit state due to the absence of resistance R5 in FIG. 6B, and magnetizing circuit 38 may provide a first known resistance (e.g., RV=R1) across first node 44A and second node 44B that may be read by an interrogating circuit such as controller 32. On the other hand, when one or more chips 50 are captured by chip detector 328 and electrically bridge gap G, chip detection circuit 48 may be closed due to the presence of resistance R5 in FIG. 6B. In this situation, the combination of magnetizing circuit 38 and of chip detection circuit 48 arranged in parallel may provide a second resistance (e.g., RV=R1∥R3+R4+R5) across first node 44A and second node 44B that may be read by the interrogating circuit such as controller 32. Such change in resistance value RV measured across first node 44A and second node 44B may be interpreted by controller 32 as a legitimate capture of one or more chips 50 and may cause annunciation 34 to be generated.

Figure 8:
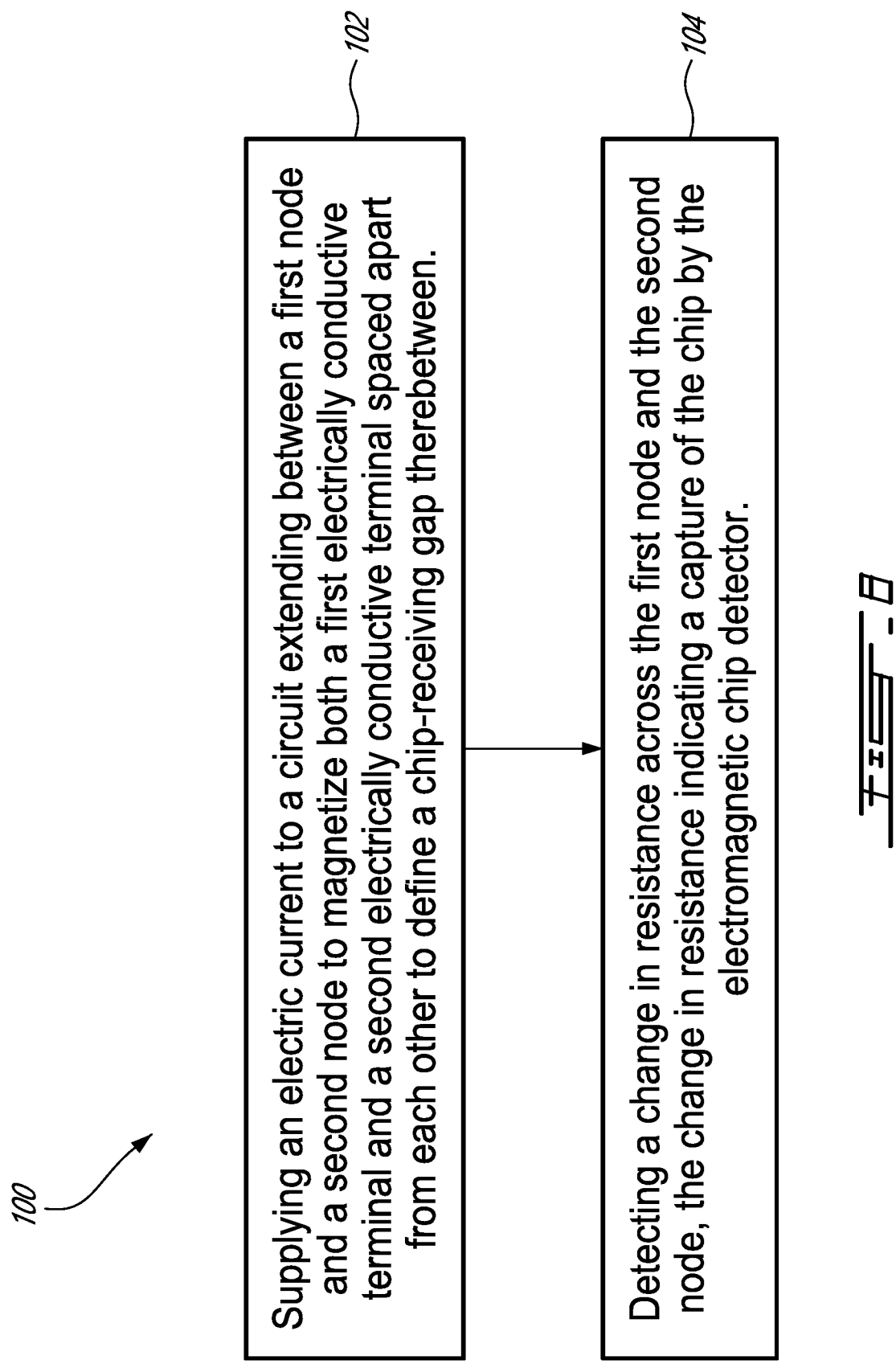
FIG. 8 is a flow diagram of a method of detecting a metallic chip in engine fluid of an engine using an electromagnetic chip detector.

FIG. 8 is a flow diagram of method 100 of detecting one or more metallic chips 50 in engine fluid of engine 10. Method 100 may be performed using any one of chip detectors 28, 128, 228 and 328, or with another chip detector. Method 100 may include other steps or actions disclosed herein. Method 100 may include elements of chip detectors 28, 128, 228 and 328. In various embodiments, method 100 may include:

supplying an electric current to magnetizing circuit 38 extending between first node 44A and second node 44B to magnetize both first terminal 36A and second terminal 36B spaced apart from each other to define gap G therebetween (block 102); and detecting a change in resistance value RV across first nodes 44A and second node 44B, the change in resistance value RV being indicative of a capture of chip(s) 50 by chip detector 28, 128, 228, 328, chip(s) 50 electrically connecting first terminal 36A to second terminal 36B, first terminal 36A being electrically connected to first node 44A, and second terminal 36B being electrically connected to second node 44B (block 104).

In some embodiments, method 100 may include altering a magnetization of first terminal 36A and of second terminal 36B after the capture of chip(s) 50 by chip detectors 28, 128, 228, 328. In some embodiments, altering the magnetization of first terminal 36A and of second terminal 36B may include reducing the magnetization of first terminal 36A and of second terminal 36B of chip detectors 28, 128, 328 for example. In some embodiments, altering the magnetization of first terminal 36A and of second terminal 36B may include increasing the magnetization of first terminal 36A and of second terminal 36B of chip detectors 228, 328 for example.

The embodiments described in this document provide non-limiting examples of possible implementations of the present technology. Upon review of the present disclosure, a person of ordinary skill in the art will recognize that changes may be made to the embodiments described herein without departing from the scope of the present technology.

What is claimed is:

1. An electromagnetic chip detector for detecting a metallic chip in lubricating fluid of an engine, the electromagnetic chip detector comprising:
    a first electrically conductive terminal;
    a second electrically conductive terminal spaced apart from the first electrically conductive terminal to define a chip-receiving gap therebetween;
    a magnetizing circuit including:
        a first coil inductively coupled to the first electrically conductive terminal to generate a first generated magnetic field of a first polarity; and
        a second coil inductively coupled to the second electrically conductive terminal to generate a second generated magnetic field of a second polarity opposite the first polarity, the first coil and the second coil being electrically connected in series between a first node and a second node;
    a chip detection circuit in parallel with the magnetizing circuit, the chip detection circuit including:
        the first electrically conductive terminal electrically connected to the first node;
        the second electrically conductive terminal electrically connected to the second node; and
        the chip-receiving gap defined between the first electrically conductive terminal and the second electrically conductive terminal.

2. The electromagnetic chip detector as defined in claim 1, wherein the first electrically conductive terminal is non-magnetized in an absence of the first generated magnetic field.

3. The electromagnetic chip detector as defined in claim 2, wherein the second electrically conductive terminal is non-magnetized in an absence of the second generated magnetic field.

4. The electromagnetic chip detector as defined in claim 1, wherein:
    the first electrically conductive terminal is a first permanent magnet having a first persistent magnetic field; and
    the first generated magnetic field supplements the first persistent magnetic field.

5. The electromagnetic chip detector as defined in claim 4, wherein:
    the second electrically conductive terminal is a second permanent magnet having a second persistent magnetic field; and
    the second generated magnetic field supplements the second persistent magnetic field.

6. The electromagnetic chip detector as defined in claim 1, wherein:
    the first electrically conductive terminal is a first permanent magnet having a first persistent magnetic field; and the first generated magnetic field opposes the first persistent magnetic field.

7. The electromagnetic chip detector as defined in claim 6, wherein:
the second electrically conductive terminal is a second permanent magnet having a second persistent magnetic field; and
the second generated magnetic field opposes the second persistent magnetic field.

8. The electromagnetic chip detector as defined in claim 1, comprising a power source supplying electric current to both the magnetizing circuit and the chip detection circuit via the first node and the second node when a chip electrically connects the first electrically conductive terminal to the second electrically conductive terminal.

9. An electromagnetic chip detector for detecting a metallic chip in engine fluid of an engine, the electromagnetic chip detector comprising:
a first electrically conductive terminal;
a second electrically conductive terminal spaced apart from the first electrically conductive terminal to define a chip-receiving gap therebetween;
a first circuit magnetizing the first electrically conductive terminal to have a first polarity and magnetizing the second electrically conductive terminal to have a second polarity opposite the first polarity;
a second circuit detecting a presence of a chip electrically connecting the first electrically conductive terminal and the second electrically conductive terminal together; and
a power source supplying electric current to both the first circuit and the second circuit via a first node and a second node when the chip electrically connects the first electrically conductive terminal to the second electrically conductive terminal.

10. The electromagnetic chip detector as defined in claim 9, comprising a magnetic core extending between the first electrically conductive terminal and the second electrically conductive terminal, the first circuit including a coil inductively coupled to the magnetic core to generate a generated magnetic field.

11. The electromagnetic chip detector as defined in claim 10, wherein the first electrically conductive terminal and the second electrically conductive terminal are both disk-shaped.

12. The electromagnetic chip detector as defined in claim 10, wherein the magnetic core is made of a non-magnetized material.

13. The electromagnetic chip detector as defined in claim 10, wherein:
the magnetic core is a permanent magnet producing a persistent magnetic field; and
the generated magnetic field supplements the persistent magnetic field.

14. The electromagnetic chip detector as defined in claim 10, wherein:
the magnetic core is a permanent magnet producing a persistent magnetic field; and
the generated magnetic field opposes the persistent magnetic field.

15. The electromagnetic chip detector as defined in claim 9, wherein the first circuit includes:
a first coil inductively coupled to a first prong defining the first electrically conductive terminal; and
a second coil inductively coupled to the a second prong defining the second electrically conductive terminal, the first coil and the second coil being electrically connected in series between the first node and the second node.

16. The electromagnetic chip detector as defined in claim 9, comprising a controller operatively connected to the electromagnetic chip detector, the controller detecting an electric resistance across the first node and the second node.

17. A method of detecting a metallic chip in engine fluid of an engine using an electromagnetic chip detector, the method comprising:
supplying an electric current to a circuit extending between a first node and a second node to magnetize both a first electrically conductive terminal and a second electrically conductive terminal spaced apart from each other to define a chip-receiving gap therebetween; and
detecting a change in resistance across the first node and the second node, the change in resistance being indicative of a capture of the metallic chip by the electromagnetic chip detector, the metallic chip electrically connecting the first electrically conductive terminal to the second electrically conductive terminal, the first electrically conductive terminal being electrically connected to the first node, and the second electrically conductive terminal being electrically connected to the second node.

18. The method as defined in claim 17, comprising altering a magnetization of the first electrically conductive terminal and of the second electrically conductive terminal after the capture of the metallic chip by the electromagnetic chip detector.

19. The method as defined in claim 18, wherein altering the magnetization of the first electrically conductive terminal and of the second electrically conductive terminal includes reducing the magnetization of the first electrically conductive terminal and of the second electrically conductive terminal.

20. The method as defined in claim 18, wherein altering the magnetization of the first electrically conductive terminal and of the second electrically conductive terminal includes increasing the magnetization of the first electrically conductive terminal and of the second electrically conductive terminal.

* * * * *